United States Patent
Akhtman et al.

(10) Patent No.: US 10,274,420 B2
(45) Date of Patent: Apr. 30, 2019

(54) COMPACT MULTIFUNCTIONAL SYSTEM FOR IMAGING SPECTROSCOPY

(71) Applicant: ECOLE POLYTECHNIQUE FEDERAL DE LAUSANNE (EPFL), Lausanne (CH)

(72) Inventors: Yosef Akhtman, Saint-Prex (CH); Dragos Constantin, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 95 days.

(21) Appl. No.: 15/326,511

(22) PCT Filed: Jul. 24, 2015

(86) PCT No.: PCT/IB2015/055614
§ 371 (c)(1),
(2) Date: Jan. 16, 2017

(87) PCT Pub. No.: WO2016/012980
PCT Pub. Date: Jan. 28, 2016

(65) Prior Publication Data
US 2017/0205337 A1     Jul. 20, 2017

(30) Foreign Application Priority Data

Jul. 24, 2014   (WO) .................. PCT/IB2014/063366

(51) Int. Cl.
*G01J 3/02*     (2006.01)
*G01N 21/31*    (2006.01)
(Continued)

(52) U.S. Cl.
CPC ............. *G01N 21/31* (2013.01); *G01J 3/027* (2013.01); *G01J 3/0229* (2013.01);
(Continued)

(58) Field of Classification Search
CPC ...... G01J 3/02; G01J 3/00; G06K 9/00; G06T 17/05; G02B 5/20; H04N 5/238;
(Continued)

(56) References Cited

U.S. PATENT DOCUMENTS 5,379,065 A   1/1995  Cutts
8,027,041 B1  9/2011  Mitchell et al.
(Continued)

FOREIGN PATENT DOCUMENTS

WO   WO2011064403 A1   6/2011
WO   WO2014063117 A1   4/2014

OTHER PUBLICATIONS

A. Wagadarikar, R. John, R. Willett, and David Brady, (2008) Single disperser design for coded aperture snapshot spectral imaging, Appl. Opt. 47, B44-B51.

(Continued)

*Primary Examiner* — Abdullahi Nur
(74) *Attorney, Agent, or Firm* — Andre Roland S.A.; Nikolaus Schibli

(57) ABSTRACT

A method for obtaining spectral imaging data comprises at least the steps of receiving a sample set of data generated by sampling a spectral property of an image of an object in a spatial basis, wherein the sampling of the spectral property of the image of the object comprises providing a Spectral Filter Array (SFA) by arranging a plurality of SFA elements together to form a surface; configuring each SFA element of the plurality of SFA elements to filter one or more spectral bandwidths centered each at specific wavelengths corresponding to that SFA element, whereby all of the plurality of SFA elements taken together cover a determined spectral range; and setting the specific wavelengths of each SFA element of the plurality of SFA elements on the surface such to obtain a uniform and aperiodic spatial distribution of all (Continued)

of the plurality of SFA elements across the surface. The sampling of the spectral property of the image of the object further comprises providing an image sensor configured to record at each pixel the light filtered by one of the plurality of SFA elements or a subset of the plurality of SFA elements thereby producing one intensity value of light filtered by the one of the plurality of elements or the subset of the plurality of SFA elements per pixel; forming the image of the object on the SFA through a lens or group of lenses; and recording for all of the pixels of the image sensor the spectrally filtered intensity values thereby obtaining a 2-dimensional array of the intensity values corresponding to the image of the object. The method for obtaining spectral imaging data further comprises the step of reconstructing a full 3 dimensional spectral data cube of the imaged object from the sampled 2-dimensional array.

13 Claims, 13 Drawing Sheets

(51) Int. Cl.
    *G01J 3/28*     (2006.01)
    *G06K 9/00*     (2006.01)
    *H04N 13/214*     (2018.01)
    *G06T 17/05*     (2011.01)

(52) U.S. Cl.
    CPC .......... *G01J 3/2823* (2013.01); *G06K 9/0063* (2013.01); *G06K 9/00657* (2013.01); *G06T 17/05* (2013.01); *H04N 13/214* (2018.05); *G01J 2003/2826* (2013.01); *G06K 2009/00644* (2013.01)

(58) Field of Classification Search
    CPC .... H04N 13/214; H04N 5/2256; H04N 5/332; G01N 21/31
    See application file for complete search history.

(56) References Cited

U.S. PATENT DOCUMENTS

| | | |
|---|---|---|
| 2003/0193589 A1 | 10/2003 | Lareau et al. |
| 2011/0142339 A1 | 6/2011 | Singh |
| 2012/0081511 A1 | 4/2012 | Kasunic et al. |
| 2015/0177429 A1* | 6/2015 | Darty ................ A61B 5/0075 348/342 |

OTHER PUBLICATIONS

Beck, A., Teboulle, M., (2009) Fast Gradient-Based Algorithms for Constrained Total Variation Image Denoising and Deblurring Problems, IEEE Transactions on Image Processing, vol. 18, No. 11, pp. 2419,2434, Nov. 2009.
Ellis, J., (2001) Searching for oil seeps and oil-impacted soil with hyperspectral imagery, Earth Observation Magazine.
Golbabaee, M., Vandergheynst, P., (2012) Hyperspectral image compressed sensing via low-rank and joint-sparse matrix recovery, IEEE International Conference on Acoustics, Speech and Signal Processing (ICASSP), p. 2741-2744.
Heikki, S., Ville-Veikko, A., Altti A., Tapani A., Christer H., Uula K., Jussi M., Jyrki O., (2009) Novel miniaturized hyperspectral sensor for UAV and space applications. Proc. SPIE 7474, Sensors, Systems, and Next-Generation Satellites XIII, 74741M, doi:10.1117/12.830284.
International Search Report of PCT/IB2015/055614 dated Nov. 4, 2015.
Lacar, F.M., et al., (2001) Use of hyperspectral imagery for mapping grape varieties in the Barossa Valley, South Australia, Geoscience and remote sensing symposium (IGARSS'01)—IEEE 2001 International, vol. 6 2875-2877.
Lustig et al, (2007) Sparse MRI: The Application of Compressed Sensing for Rapid MR Imaging, MRM 58:1182-1195.
Subhasis, S., (2000) Image compression—from DCT to wavelets: a review. Crossroads 6, doi:10.1145/331624.331630.
T. M. Mitchell, "Machine Learning", 1997, McGraw-Hill. ISBN: 0070428077 9780070428072.
The Economic Impact of Unmanned Aircraft Systems Integration in the United States, AUVSI, 2013.
Written Opinion of the International Search Authority dated Nov. 4, 2015.
Communication under Article 94(3) EPC from a counterpart application of the EPO with the Serial No. 15 767 257.7 , dated Jan. 9, 2018.

* cited by examiner

| 580 | 780 | 850 | 550 | 950 | 590 | 740 | 750 | 700 | 770 | 820 | 870 |
|---|---|---|---|---|---|---|---|---|---|---|---|
| 930 | 590 | 820 | 980 | 700 | 850 | 830 | 610 | 770 | 850 | 540 | 750 |
| 710 | 440 | 590 | 780 | 430 | 740 | 700 | 890 | 590 | 460 | 780 | 670 |
| 650 | 930 | 430 | 470 | 870 | 760 | 860 | 520 | 840 | 510 | 880 | 870 |
| 900 | 990 | 790 | 490 | 990 | 420 | 490 | 870 | 800 | 820 | 540 | 730 |
| 850 | 510 | 550 | 800 | 840 | 570 | 920 | 760 | 920 | 710 | 410 | 630 |
| 500 | 970 | 510 | 700 | 1000 | 780 | 580 | 620 | 610 | 590 | 760 | 560 |
| 450 | 610 | 880 | 440 | 820 | 940 | 920 | 960 | 850 | 500 | 980 | 990 |
| 540 | 440 | 770 | 840 | 800 | 440 | 550 | 820 | 430 | 960 | 620 | 930 |
| 750 | 670 | 900 | 650 | 880 | 930 | 530 | 660 | 570 | 400 | 440 | 540 |
| 470 | 510 | 660 | 840 | 900 | 980 | 870 | 940 | 840 | 720 | 920 | 770 |
| 510 | 950 | 520 | 750 | 810 | 580 | 620 | 720 | 420 | 660 | 480 | 460 |

Fig. 3A

| 430 | 580 | 840 | 750 | 820 | 410 | 570 | 800 | 560 | 780 | 400 | 670 |
|---|---|---|---|---|---|---|---|---|---|---|---|
| 860 | 950 | 420 | 630 | 530 | 630 | 400 | 690 | 770 | 870 | 950 | 800 |
| 650 | 520 | 710 | 860 | 740 | 900 | 670 | 820 | 430 | 620 | 540 | 590 |
| 750 | 730 | 970 | 430 | 850 | 570 | 410 | 950 | 920 | 860 | 520 | 980 |
| 710 | 940 | 700 | 580 | 630 | 780 | 830 | 770 | 720 | 510 | 480 | 820 |
| 470 | 930 | 680 | 890 | 1000 | 500 | 570 | 760 | 580 | 670 | 510 | 960 |
| 720 | 840 | 620 | 400 | 510 | 840 | 800 | 680 | 790 | 460 | 690 | 620 |
| 590 | 910 | 960 | 800 | 840 | 980 | 490 | 980 | 520 | 920 | 750 | 910 |
| 790 | 860 | 540 | 620 | 560 | 720 | 770 | 840 | 580 | 980 | 820 | 910 |
| 530 | 430 | 660 | 880 | 410 | 820 | 790 | 600 | 520 | 660 | 690 | 1000 |
| 880 | 730 | 690 | 570 | 880 | 950 | 780 | 500 | 570 | 600 | 660 | 860 |
| 580 | 440 | 650 | 530 | 850 | 740 | 1000 | 860 | 690 | 550 | 910 | 890 |

Fig. 3B

| 580 | 780 | 850 | 550 | 950 | 590 | 740 | 750 | 700 | 770 | 820 | 870 |
|---|---|---|---|---|---|---|---|---|---|---|---|
| 930 |  | 820 |  | 700 |  | 830 |  | 770 |  | 540 |  |
| 710 | 440 | 590 | 780 | 430 | 740 | 700 | 890 | 590 | 460 | 780 | 670 |
| 650 |  | 430 |  | 870 |  | 860 |  | 840 |  | 880 |  |
| 900 | 990 | 790 | 490 | 990 | 420 | 490 | 870 | 800 | 820 | 540 | 730 |
| 850 |  | 550 |  | 840 |  | 920 |  | 920 |  | 410 |  |
| 500 | 970 | 510 | 700 | 1000 | 780 | 580 | 620 | 610 | 590 | 760 | 560 |
| 450 |  | 880 |  | 820 |  | 920 |  | 850 |  | 980 |  |
| 540 | 440 | 770 | 840 | 800 | 440 | 550 | 820 | 430 | 960 | 620 | 930 |
| 750 |  | 900 |  | 880 |  | 530 |  | 570 |  | 440 |  |
| 470 | 510 | 660 | 840 | 900 | 980 | 870 | 940 | 840 | 720 | 920 | 770 |
| 510 |  | 520 |  | 810 |  | 620 |  | 420 |  | 480 |  |

Fig. 3C

COMPACT MULTIFUNCTIONAL SYSTEM FOR IMAGING SPECTROSCOPY

CROSS REFERENCE TO RELATED APPLICATIONS

The present application is a U.S. national stage application of PCT/IB2015/055614 filed on Jul. 24, 2015 designating the United States, and claims foreign priority to International patent application PCT/IB2014/063366 filed on Jul. 24, 2014, the contents of both documents being herewith incorporated by reference in their entirety.

TECHNICAL FIELD OF INVENTION

The invention relates to the field of imaging spectroscopy, and more precisely hyperspectral imaging. More specifically, the invention comprises a compressive spectral image acquisition and reconstruction system.

BACKGROUND OF INVENTION

Imaging Spectroscopy

Imaging spectroscopy is a digital sensing process in which a scene is optically sampled in two spatial dimensions and in one spectral dimension, producing a three dimensional data cube. Spectral images contain significantly larger amount of spectral information than color photography, typically comprising tens or hundreds of well defined narrow spectral channels for each individual pixel of the image. In other words each spatial pixel of the spectral image contains a spectral response of the respective point of the imaged surface. In comparison, a color image is comprised by three loosely defined Red-Green-Blue channels. Spectral images further distinguish themselves from color photography through the rigorously measured radiometric output: while color is perception based and has no absolute units, spectral radiance is a physical measure whose unit is $[Wm^{-2} \mu m^{-1} sr^{-1}]$. As a consequence, spectral imaging is often used to determine the chemical and biological composition of objects, while avoiding the need for physical contact [1, 2]. The acquisition of 3D hyperspectral imaging data is difficult because of the two-dimensional nature of the imaging sensors.

In order to obtain the spectral data cube with a two dimensional sensor, most spectral imaging cameras use the following three elements:
1. An optical element, such as a lens: to focus the optical scene onto an imaging plane.
2. A dispersive element, such as a prism or diffraction grid: to spatially distribute spectral information from the imaging plane.
3. An imaging sensor, such as a CCD or a CMOS: to spatially sample the dispersed light.

Due to the spectral dispersion, spatial resolution must be compromised. To overcome the resolution loss, many spectral imaging cameras employ some form of scanning:

Pushbroom, or line-scan, cameras capture a spatio-spectral slice of the datacube, using the two dimensions of the imaging sensor as 1D spectral and 1D spatial sampling. Pushbroom sensors require movement to reconstruct an entire hyperspectral image, they require spatial scanning.

Band sequential cameras capture a spectral slice of the spectral data cube, using either rotating or tunable spectral filters. They use the two dimensions of the imaging sensor as 2D spatial sampling and scan spectrally by sequentially applying different spectral filters in front of the imaging sensor, they thus require spectral scanning.

Interferometry-based spectral cameras sequentially capture interferograms of the data cube onto the image sensor. The interferograms are generated by tuning an interferometer, a process similar to spectral scanning.

Frame, or snapshot, spectral cameras acquire the entire data cube without scanning, severely compromising resolution. State-of-the-art snapshot spectral cameras are either based on 2D diffraction grids or small filter banks, requiring a high resolution sensor and producing very low resolution spectral data cubes with respect to scanning spectral cameras [2].

Compressive Sensing

Classical signal processing dictates that in order to sample, then reconstruct a signal without information loss, the signal has to be sampled with at least twice the highest frequency it contains. This minimal sampling frequency is also called Nyquist frequency. If sampling is done under the Nyquist frequency, the reconstructed signal will show information loss and artefacts such as aliases. The large number of measurements required to reconstruct a full hyperspectral data cube under the Nyquist constraint is one of the main reasons why all non-compressive snapshot spectral cameras have low resolution.

Recent research in signal processing and advances in computational power have led to many improvements in signal acquisition bandwidth reduction through compressive sensing. At the core of compressive sensing lays the hypothesis that if the signal that needs to be acquired is sparse in some mathematical basis, the number of measurements required to reconstruct the signal are given by its sparsity and can thus be significantly smaller than the number of measurements dictated by the Nyquist frequency.

The effective reconstruction of the original signal using the compressive sensing mathematical models imposes certain requirements on the underlying signal sampling methodology, in particular uniformity and aperiodicity.

In areas of applications such as magnetic resonance imaging (MRI), compressive sensing has been successfully implemented in order to reduce the amount of required measurements by a factor of between 10 and 20 [4], or, with a corresponding compression ratio of between 1/10 and 1/20. For color images, the method has been suggested in [5], but the practical implementation has been limited by the low information gain and high computational cost with respect to classical demosaicing. In color photography, the required compression ratios is 1/3 as the images have a small quantity of spectral information.

Compressive sensing has also been applied to spectral imaging in multiple scientific experiments, showing compression ratios of between 1/4 and 1/16, [6][7]. These experiments, however, failed to produce the results needed for a practical snapshot spectral camera which requires compression ratios around 1/50 or more. The color imaging methods described in [5] cannot be directly applied to 2D spectral sampling-based imaging for a plurality of reasons:

Correct pixel-wise spectral reconstruction poses a series of new challenges such as optimal spectral distribution of filters, or higher order filter response cancellation.

Color filter arrays do not provide sufficient spectral separation

For hyperspectral image reconstruction, the algorithms need to reconstruct a significantly larger set of data from less than 5% of its size, as opposed to 33% subsampling rate of color imaging.

Interferometric Spectral Filter Array

Due to the very stringent requirements of spectral imaging, a spectral filter array is much more difficult to produce than the color arrays used in commercial color cameras. Color cameras generally employ pigment-based filters whose spectral transmission bandwidth is too wide and irregular for the radiometric measurements of spectral imaging. The number of different filters that can be produced in a pigment-based color filter array is also limited by the number of pigments used. The cost of a color filter array thus greatly increases with the increase in the number of different filters.

Interferometric filters, such as Fabry-Perot filters, are based on a different principle than pigment filters and enjoy a number of properties useful for imaging spectroscopy:

finely tunable central wavelength: the central wavelength is given by the distance between the reflective surfaces used to make light interfere with itself. Varying this distance changes the central wavelength of the filter without significantly altering the shape of its spectral transmission curve;

symmetry around central wavelength: the filter transmission is locally symmetric with respect to the central wavelength, due to the natural interferometric process;

finely tunable bandwidth: the filter bandwidth is given by the reflectivity of the surfaces which reflect the light;

the production cost of a large number of different wavelength interferometric filters is much lower than for pigment-based filters.

While their properties make them an obvious choice for imaging spectroscopy, until recently, interferometric filters were not feasible to create at the size of a single pixel. Fabry-Perot filters were thus used to produce spectral images by band-sequential scanning, as large global filters, which cover the entire sensor surface [8]. However, recent developments in miniaturization and nanotechnology have led to the development of interferometric spectral filter arrays with the individual filters being no larger than a pixel [4].

One of the main disadvantages of interferometric filters is their second and higher order transmissions. These higher order transmissions of the filters let light pass not only at the desired central wavelength, but also at twice that wavelength, three times that wavelength and so on. Interferometric filters can also be configured as multiband filters, due to the higher order transmissions which include multiple specific wavelengths for which they transmit light. In most cases, the higher order transmissions are undesired effects and need to be nullified.

SUMMARY OF THE INVENTION

In a first aspect, the invention provides a method for obtaining spectral imaging data. The method comprises at least the steps of receiving a sample set of data generated by sampling a spectral property of an image of an object in a spatial basis, wherein the sampling of the spectral property of the image of the object comprises providing a Spectral Filter Array (SFA) by arranging a plurality of SFA elements together to form a surface; configuring each SFA element of the plurality of SFA elements to filter one or more spectral bandwidths centered each at specific wavelengths corresponding to that SFA element, whereby all of the plurality of SFA elements taken together cover a determined spectral range; and setting the specific wavelengths of each SFA element of the plurality of SFA elements on the surface such to obtain a uniform and aperiodic spatial distribution of all of the plurality of SFA elements across the surface. The sampling of the spectral property of the image of the object further comprises providing an image sensor configured to record at each pixel the light filtered by one of the plurality of SFA elements or a subset of the plurality of SFA elements thereby producing one intensity value of light filtered by the one of the plurality of elements or the subset of the plurality of SFA elements per pixel; forming the image of the object on the SFA through a lens or group of lenses; and recording for all of the pixels of the image sensor the spectrally filtered intensity values thereby obtaining a 2-dimensional array of the intensity values corresponding to the image of the object. The method for obtaining spectral imaging data further comprises the step of reconstructing a full 3 dimensional spectral data cube of the imaged object from the sampled 2-dimensional array.

In a preferred embodiment the step of reconstructing comprises a mathematical modelling and computational numerical optimization.

In a further preferred embodiment, the mathematical modelling and computational numerical optimization comprises a machine learning method which enables an absence of transmission measurement by the SFA.

In a further preferred embodiment, the mathematical modelling and computational numerical optimization comprises at least a convex optimization method based on transmission measurement of the SFA.

In a further preferred embodiment, the step of reconstructing comprises providing measured transmissions of individual SFA elements of the SFA; creating a system design matrix from measured transmissions of individual SFA elements and image sensor radiometric calibration; and inferring non sampled spectral information using deconvolution or non-linear sparse reconstruction methods based on the system design matrix.

In a further preferred embodiment, the step of setting the specific wavelengths of each SFA element of the plurality of SFA elements on the surface such to obtain the uniform and aperiodic spatial distribution of the specific wavelengths of the SFA is deterministic, thereby comprising an aperiodic tiling such as Wang or Penrose.

In a further preferred embodiment, the step of setting the specific wavelengths of each SFA element of the plurality of SFA elements on the surface such to obtain the uniform and aperiodic spatial distribution of the specific wavelengths of the SFA further comprises filling the SFA surface with a repeating pattern, then continuously and randomly interchanging the SFA elements until the measured entropy of the SFA central wavelengths is sufficiently high.

In a further preferred embodiment, the step of setting the specific wavelengths of each SFA element of the plurality of SFA elements on the surface such to obtain the uniform and aperiodic spatial distribution of the specific wavelengths of the SFA further comprises a random sampling of the SFA elements from a uniform distribution.

In a further preferred embodiment, the step of setting the specific wavelengths of each SFA element of the plurality of SFA elements on the surface such to obtain the multiband distribution of the specific wavelengths of the SFA further comprises a sampling of multiband SFA elements such that neighboring SFA elements are spectrally orthogonal.

In a second aspect, the invention provides a method for Spectral Filter Array (SFA) element second-degree transmission cancellation through SFA design and subsequent response subtraction. The method comprises at least designing a uniformly and aperiodically distributed Spectral Filter Array (SFA) by arranging a plurality of SFA elements together to form a surface; configuring each SFA element of the plurality of SFA elements to filter a spectral bandwidth centered at a central wavelength corresponding to that SFA element, whereby all of the plurality of elements taken together cover a determined spectral range; and setting the central wavelength of each SFA element of the plurality of SFA elements on the surface such to obtain a distribution of all the central wavelengths to be uniform and aperiodic over the surface. The method further comprises identifying the SFA elements with second degree transmission in the sensitivity range of an image sensor; changing the central wavelength of SFA elements neighboring the SFA elements with second degree transmission, as to match the central wavelength of the second degree transmission; re-arranging the SFA element central wavelengths which were not changed or do not have a second degree transmission, as to maintain the uniformity of the SFA central wavelength distribution; and in a 2-dimensional array of pixel intensity values, subtracting the response corresponding to the changed neighboring elements from the response corresponding to the SFA elements which have a second degree transmission.

In a third aspect, the invention provides a method for obtaining a real-time monochromatic preview of an imaged object, the imaged object having been obtained using the method of obtaining spectral imaging data described herein above, the method for obtaining the real-time monochromatic preview comprising designing a uniform aperiodic Spectral Filter Array (SFA) by arranging a plurality of SFA elements together to form a surface, configuring each SFA element of the plurality of SFA elements to filter a spectral bandwidth centered at a central wavelength corresponding to that SFA element, whereby all of the plurality of SFA elements taken together cover a determined spectral range, and setting the central wavelength of each SFA element of the plurality of SFA elements on the surface such to obtain a distribution of all the central wavelengths to be uniform and aperiodic over the surface; generating a subset of SFA elements by a 2-dimensional periodic selection; replacing the SFA elements belonging to the above subset with SFA elements of identical transmission; and from a 2-dimensional array of pixel intensity values, using a subset of values, corresponding to the subset of periodic SFA elements with identical transmission, to create a lower resolution monochromatic image.

In a fourth aspect, the invention provides a method for obtaining a real-time monochromatic preview of an imaged object, the imaged object having been obtained using the method of obtaining spectral imaging data described herein above, the method for obtaining the real-time monochromatic preview comprising designing a uniform aperiodic Spectral Filter Array (SFA) by arranging a plurality of SFA elements together to form a surface, configuring each SFA element of the plurality of SFA elements to filter multiple spectral bands centered at specific wavelengths corresponding to that SFA element, whereby all of the plurality of SFA elements taken together cover a determined spectral range, and setting the central wavelength of each SFA element of the plurality of SFA elements on the surface such that neighboring SFA elements are spectrally orthogonal; from a 2-dimensional array of pixel intensity values, spatially interpolating each channel corresponding to an SFA element configuration independently at pixel locations where other SFA element configurations are present; and averaging the independently interpolated channels, to create a high resolution monochromatic image.

In a fifth aspect, the invention provides a method for generating a spectral 3D-model of an imaged object and increasing the spectral reconstruction quality of an imaged scene, comprising taking multiple images of the scene, each of the images comprising at least an array of pixel intensities; using monochromatic previews to optically align the images through image registration, thus generating the 3D-model of the scene; grouping values from different ones of the arrays of pixel intensities corresponding to different images of the multiple images, if the pixels are aligned to a same point in the imaged scene; based on grouped values, re-modeling a system design matrix corresponding to multiple arrays of pixel intensities, taken from different locations; and reconstructing the spectral texture of the 3D model based on the cross-image system design matrix.

In a sixth aspect, the invention provides a computer program stored on a memory device, the computer program when executed by a computing device reading the memory device enabling to reconstruct a 3D-hyperspectral image from a 2D-spatial-spectral dataset, by implementing the steps of the method for obtaining spectral imaging data as described herein above.

A corresponding hyperspectral image reconstruction module comprises a single- or multi-processor computing device, or a computer network programmed to reconstruct a 3D hyperspectral image from a 2D dataset. The underlying algorithmic framework of the hyperspectral image reconstruction may include deconvolution, non-linear sparse reconstruction, regressive machine learning methods, projection of the acquired spectral samples onto a set of a priori known spectral signatures, as well as any combination of the herein three methods. Algorithmic methods are also provided for variable spatio-spectral resolution reconstruction of the imaged scene, based on a fixed configuration imager.

BRIEF DESCRIPTION OF THE FIGURES

The invention will be better understood in view of the description of preferred embodiments and in reference to the drawings, wherein:

FIG. 3A shows an example of a uniformly distributed and aperiodic 12×12 element spectral filter array pattern given by central wavelength in nanometers. 61 possible filters were considered with central wavelengths between 400 and 100 nm, at a step of 10 nm;

FIG. 3B is a variation of FIG. 3A where elements having a non-negligible second degree transmission are always placed in the direct vicinity of elements filtering at twice their central wavelength. These filter pairs are highlighted in gray;

FIG. 3C is a variation of FIG. 3A where the aperiodic pattern is interleaved with a periodic pattern of non-filtering elements or elements having a common spectral transmission. The elements of the periodic pattern are highlighted in gray;

DETAILED DESCRIPTION OF THE INVENTION

In this section, we outline the advantages of the presented solution with respect to prior art and subsequently focus on the technical details pertaining to three major aspects of the invention, namely:

1. the camera design and functionality;
2. the spectral filter array design; and
3. the reconstructor embodiments and preferred implementation.

The present invention improves upon prior art in multiple ways. With respect to spatial or spectral scanning spectral imaging systems, the present invention overcomes the need to scan, sampling the imaged scene simultaneously while providing similar resolution. Due to the extremely short optical path of the present invention, a much smaller and lighter spectral image acquisition system can be built than those requiring spectrally dispersive elements. The reduced complexity of the optical and mechanical parts also significantly lowers the production cost when compared to spectral imaging systems with dispersive elements. With respect to state-of-the-art snapshot spectral acquisition systems, the present invention generates significantly higher resolution spectral data cubes. The present invention greatly reduces the amount of storage required to acquire a spectral data cube as it is reconstructed from the relatively small 2D set of optical samples that does not exceed the number of pixels of the imaging sensor, while the full data cube contains as many elements as the number of pixels on the sensor multiplied by the number of registered spectral bands. The size ratio between the 2D set of samples and the reconstructed hyperspectral data cube can vary depending on the configuration, but will typically be between 1/10 and 1/200.

Camera

Figure 1A:
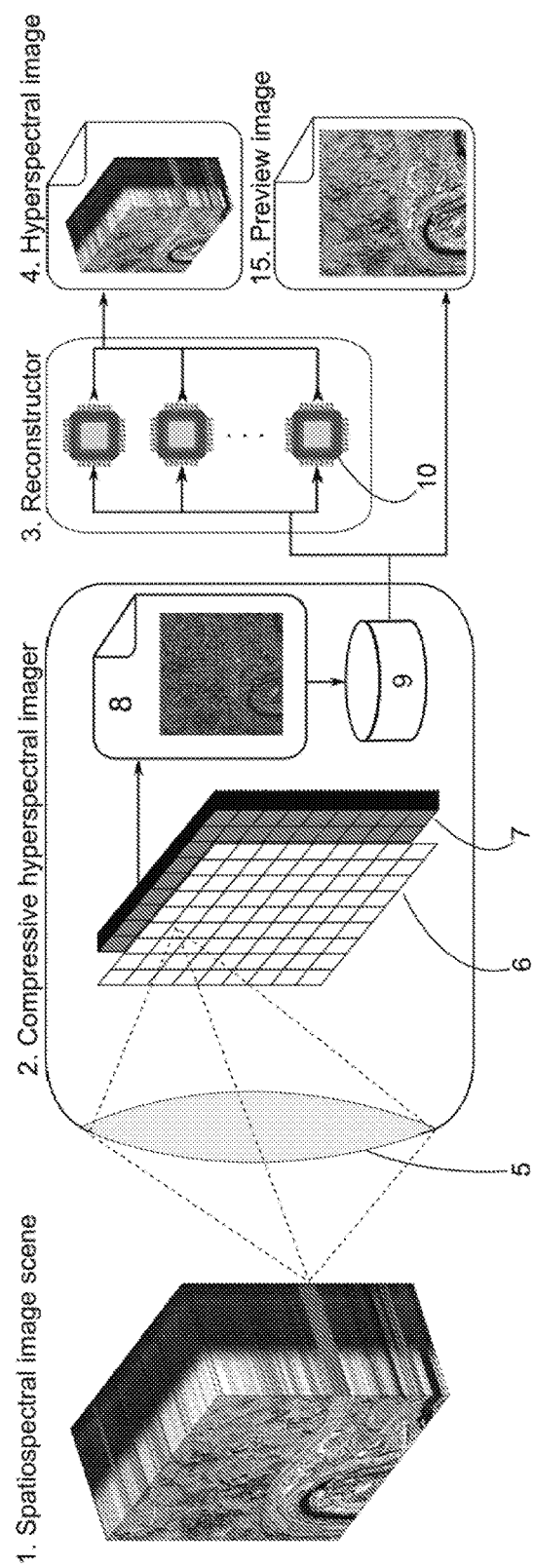
FIG. 1A is a schematic overview of the core imaging design and process.

A core embodiment of the invention comprises an imaging spectroscopy camera system depicted in FIG. 1A, employed for producing a 2D set of spectral samples 8 and a computational method which is utilized to reconstruct a complete 3D spectral data cube from the aforementioned 2D set of optical samples. More specifically, the camera comprises an optical lens 5, or a group of lenses, used for producing an image of the object of interest 1 on the image plane. The camera further comprises a spectral filter array (SFA) 6 wherein the various spectral components of the object's image are transmitted to the image sensor, and the image sensor array 7 arranged to detect the light transmitted by the individual SFA elements. The camera also contains an analog-to-digital signal converter and a storage medium 9, on which the resultant 2D datasets are stored.

The corresponding spectral data cube reconstruction module 3, or reconstructor, comprises a single- or multi-processor computing device, or a computer network programmed to reconstruct a 3D spectral image from the 2D set of optical samples.

The underlying algorithmic framework of the spectral image reconstruction may include deconvolution, non-linear sparse reconstruction, projection of the acquired spectral samples onto a set of a priori known spectral signatures, as well as any combination of the herein described three methods.

The imaging process is as follows:

The imaged scene is focused by the lens onto the plane of the SFA.

Each element of the SFA lets only certain frequencies of light pass through it, depending on its transmission curve.

Light transmitted by the SFA falls onto the imaging sensor which generates, for each pixel, an electrical charge in a manner proportional to the amount of light received by the pixel.

The electrical charges in the imaging sensor are discretized and digitized by an analog-to-digital converter, producing the sensor readout.

The sensor readouts are then stored onto the storage medium.

The reconstructor will receive the sensor readouts from the storage medium and will reconstruct the full 3D spectral image.

Figure 1B:
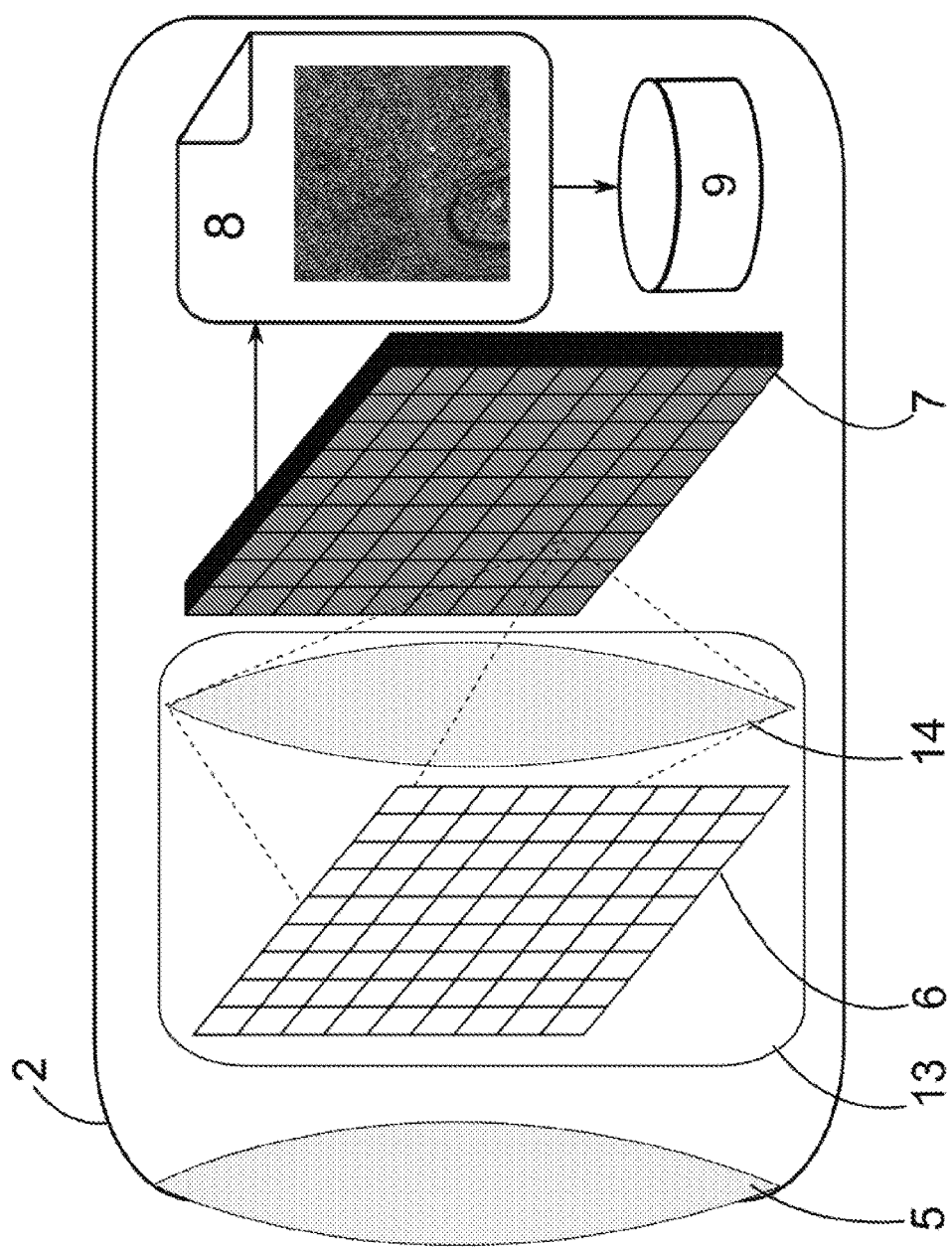
FIG. 1B is a variation of the 2D spectral sampling imager based on a spectral filter array adapter fitted between the main imaging lens and the imaging sensor.

In some embodiments, the camera of this invention is based on an interchangeable lens camera as depicted in FIG. 1B. The spectral filter array 6 and a refocusing lens 14 are built into an adapter 13 which fits in between the lens 5 and the imaging sensor 7 of the interchangeable lens camera. The image from the lens is focused on the spectral filter array, then refocused onto the imaging sensor by the refocusing lens. In these embodiments, any interchangeable lens color camera becomes the core of this invention by using such an adapter 13.

Various embodiments of the main imaging lens 5 include a fixed focal optical lens, or lens groups, while others feature a variable focal and variable focus lens.

Some embodiments see the storage medium 9 integrated in the camera while others have no storage medium, the images being sent to a computer or a computer network directly after acquisition and analog-to-digital conversion.

Spectral Filter Array

Most embodiments of the present invention include a uniformly distributed aperiodic spectral filter array 6, which we refer to as SFA, composed of individual spectral filters, referred to as elements. An example of such an SFA embodiment is shown in FIG. 3A where each element is represented by its central wavelength. In other implementations, the SFA may also contain non-filtering elements, while preserving an aperiodic distribution of interferometric filters across the majority of its surface, as shown in FIG. 3C. In the preferred implementation, the SFA is composed of interferometric filters such as Fabry-Perot filters.

The uniform aperiodic distribution may be obtained in several ways:

deterministically through aperiodic tiling such as Wang or Penrose tiling.

by filling the SFA surface with a repeating pattern, then continuously and randomly inter-changing the SFA elements until the measured entropy of the SFA central wavelengths distribution is sufficiently high.

by random sampling the SFA elements from a uniform distribution.

Figure 4:
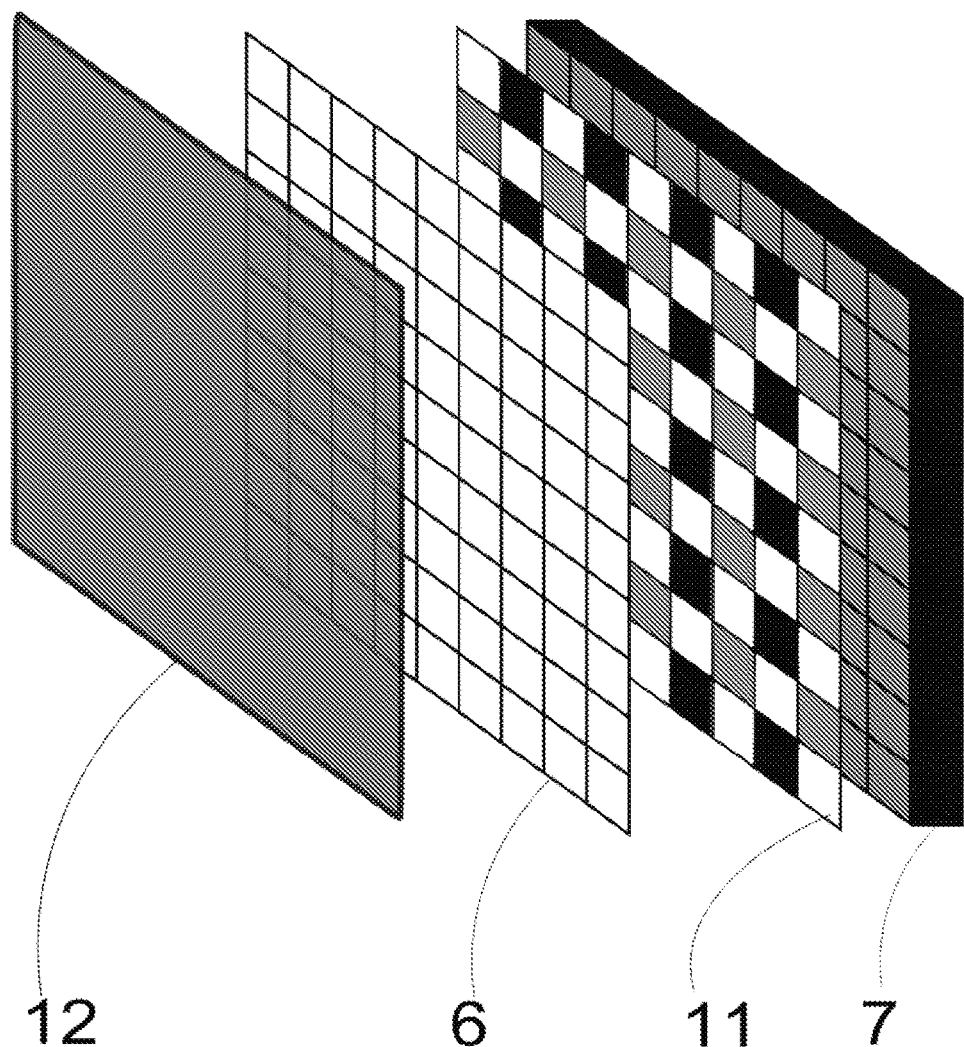
FIG. 4 depicts an image filtering configuration where the spectral filter array is preceded by an anti-aliasing filter and followed by a color filter array, along the optical path of the light to the imaging sensor.

Some embodiments of the invention include SFA designs where the second and higher degree transmissions of the interferometric spectral filters are nullified by means of several methods:

A method for second degree cancellation consists of placing the SFA 6 over an existing color filter array 11 (such as a Bayer pattern filter array), matching the individual SFA elements' transmission so that only the first order response will be transmitted by the color filter array, as shown in FIG. 4.

Another method for second order transmission cancellation is always placing a SFA element with its transmission equal to that of the second degree of one of its adjacent elements, if those filters have 2nd degree transmission in the sensitivity range of the sensor. The design depicted in FIG. 3B, allows for subtracting the second degree transmission based on adjacent filters, prior to reconstruction.

Figure 6:
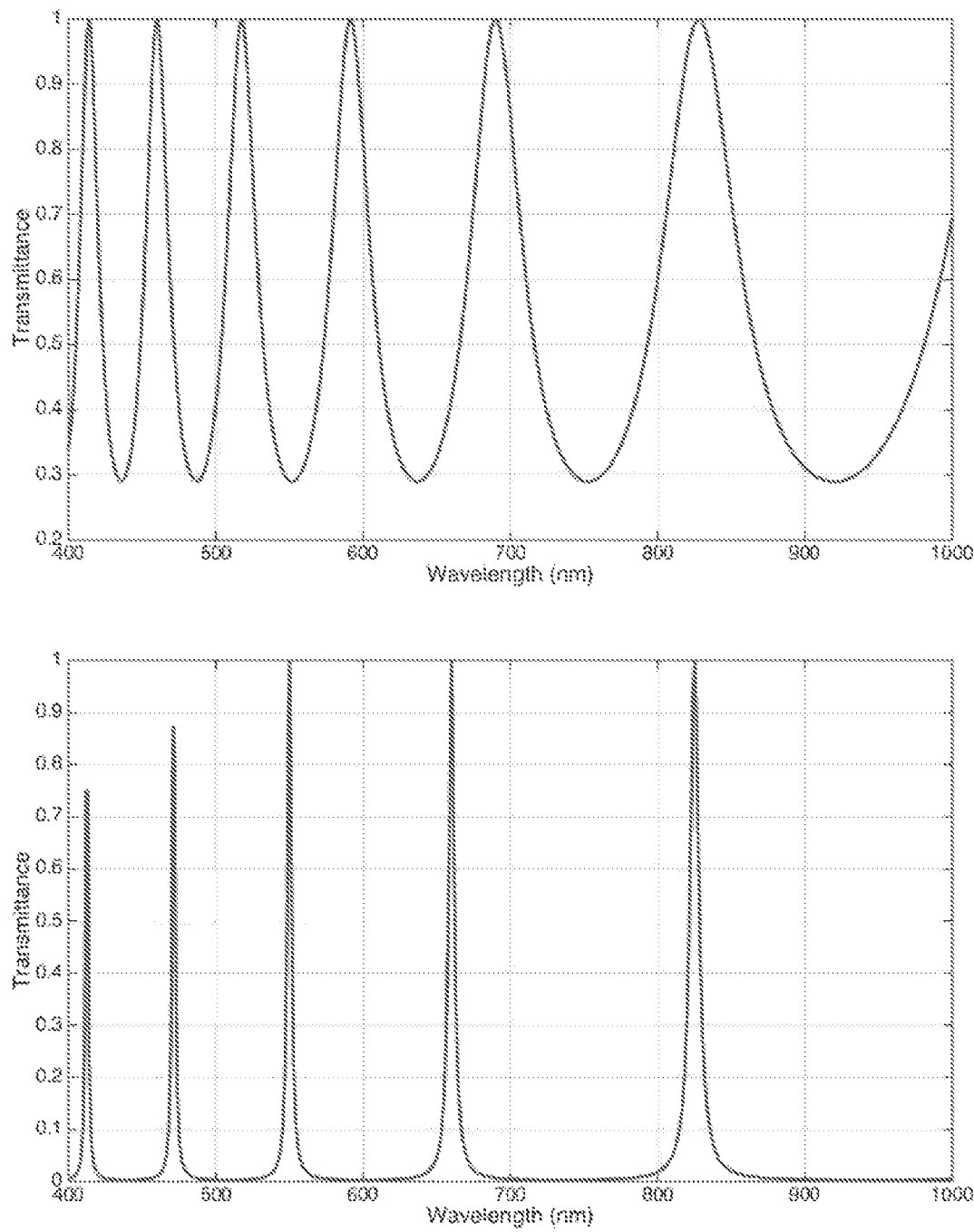
FIG. 6 shows example plots of transmissions of two Fabry-Perot spectral array elements designed for multiband filtering. Variations in both multiband wavelength number and bandwidth are illustrated. A wideband filter designed with 6 specific wavelengths (above) and a narrowband filter designed with 5 multiband wavelengths (below) are plotted.

Some embodiments of the invention use interferometric filters with multiband wavelength transmissions, rather than central wavelengths, as the elements of the SFA. Examples of these multiband filter transmissions are shown in FIG. 6. In these embodiments, the spatial uniform aperiodic distribution of the elements is chosen to maximize the spectral orthogonality of the multiband filters. By spectral orthogonality between filters we mean that they respond differently to the same wavelengths. Maximizing spectral orthogonality translates to choosing filters which do not correlate spectrally.

In various embodiments, an element at periodic positions in the SFA has the same transmission across the entire spectral filter array as shown in FIGS. 4 and 1A. This periodic element can be either an interferometric spectral filter, a pigment-based color filter, or a non-filtering element transmitting all wavelengths of light. The pixels under these periodic elements will be used to create preview images 15 of the imaged scene. These images can be used as real-time previews of the imaged scene or directly in image registration and image based 3D reconstruction.

Some embodiments of the invention include a camera where an anti-aliasing filter 12 is placed before the spectral filter array, as depicted in FIG. 4, for homogenizing the light reaching the different filters. The anti-aliasing filter may be comprised by: birefringent filters extending over more than 2×2 of the sensor elements, a defocused objective lens with a matched aperture stop, and/or a degraded imaging lens.

Spectral Cube Reconstruction

In various embodiments of the invention, the reconstructor 3 is either a single computer, a programmable single or multi-processor 10 device or a computer network programmed to reconstruct the hyperspectral image from an acquired two-dimensional dataset 8 through non-linear sparse reconstruction. The reconstructor can also be a virtual machine, accessible through the internet and ran on cloud-based computational servers.

Figure 1C:
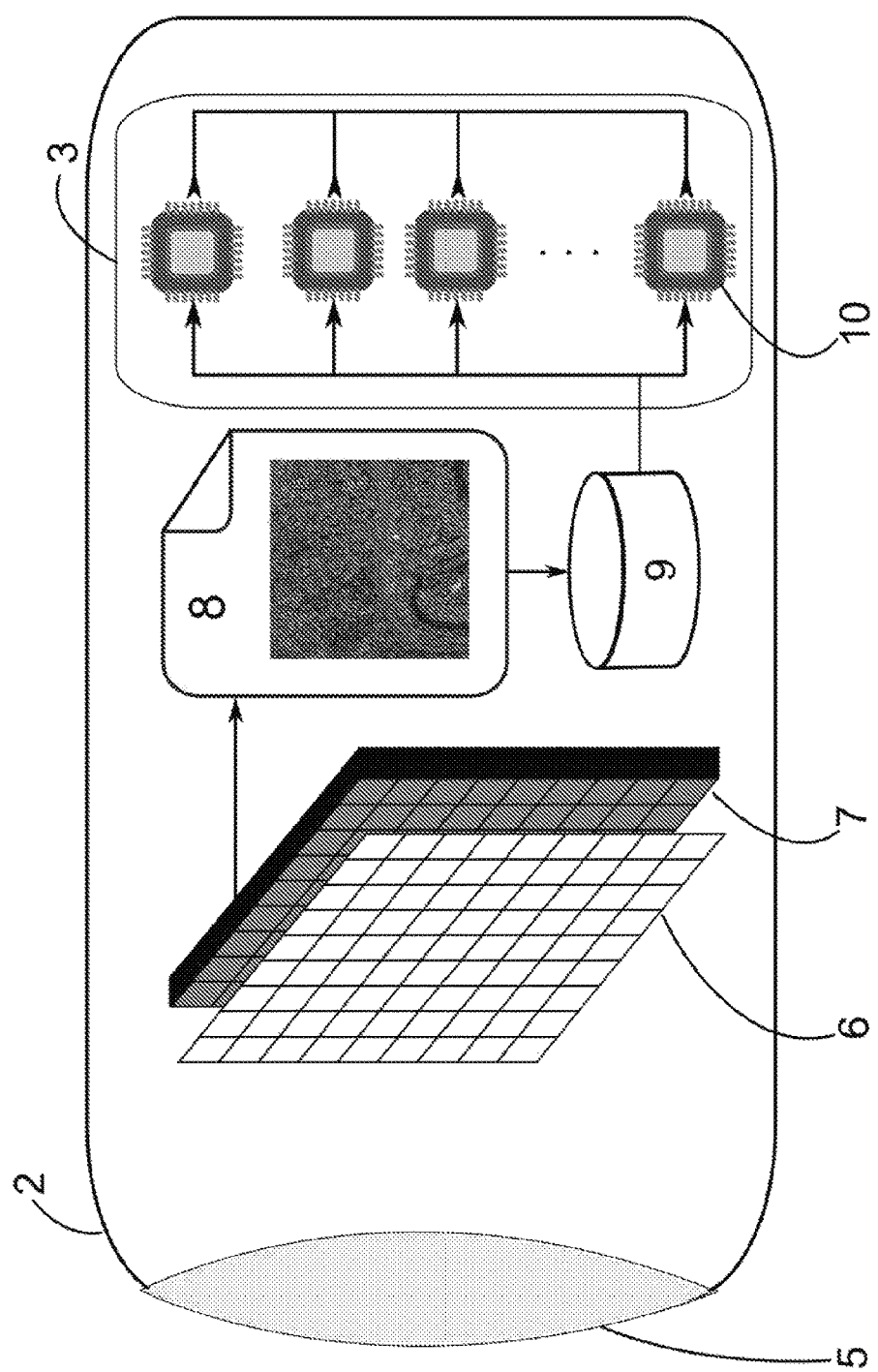
FIG. 1C is a variation of the 2D spectral sampling imager where the reconstructor is integrated into the imager.

Various embodiments feature the reconstructor integrated in the camera and producing the hyperspectral image immediately after having acquired the two-dimensional set of optical samples. FIG. 1C depicts such an integrated camera, composed of the imaging optics 5 which focus the light onto the SFA 6 that is deposited over the imaging sensor 7. Data from the imaging sensor 8 is then saved on the storage medium 9 and converted to spectral data by the reconstructor 3, composed of multiple processing units 10.

The mathematical model describing the sampling and discretization of the imaged scene by the hyperspectral imager of this invention is described by the following linear system:

$$Ax=y, \tag{1}$$

where A is the system design matrix containing the spectral transmission of the individual elements of the SFA, y is the sensor readout, and x is the hyperspectral data cube corresponding to the spatio-spectral properties of the imaged scene. Vectors x and y are thus serialized versions of the 3D hyperspectral and 2D sensor datasets.

Figure 5A:
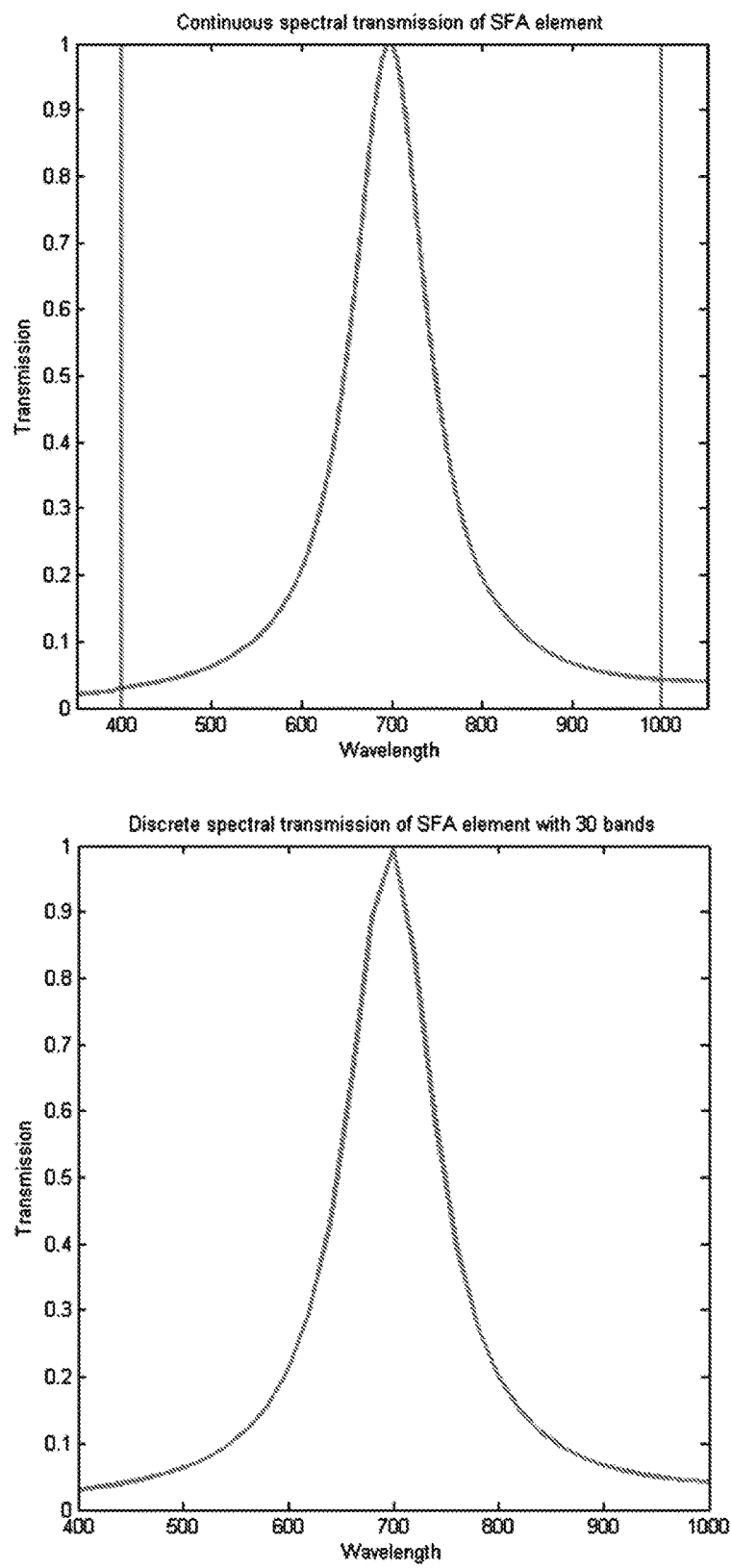
FIG. 5A-B contain example plots of the continuous and discretized spectral transmission of a Fabry-Perot spectral array element with a central wavelength of 700 nm and a full width at half maximum of 100 nm.
Figure 5B:
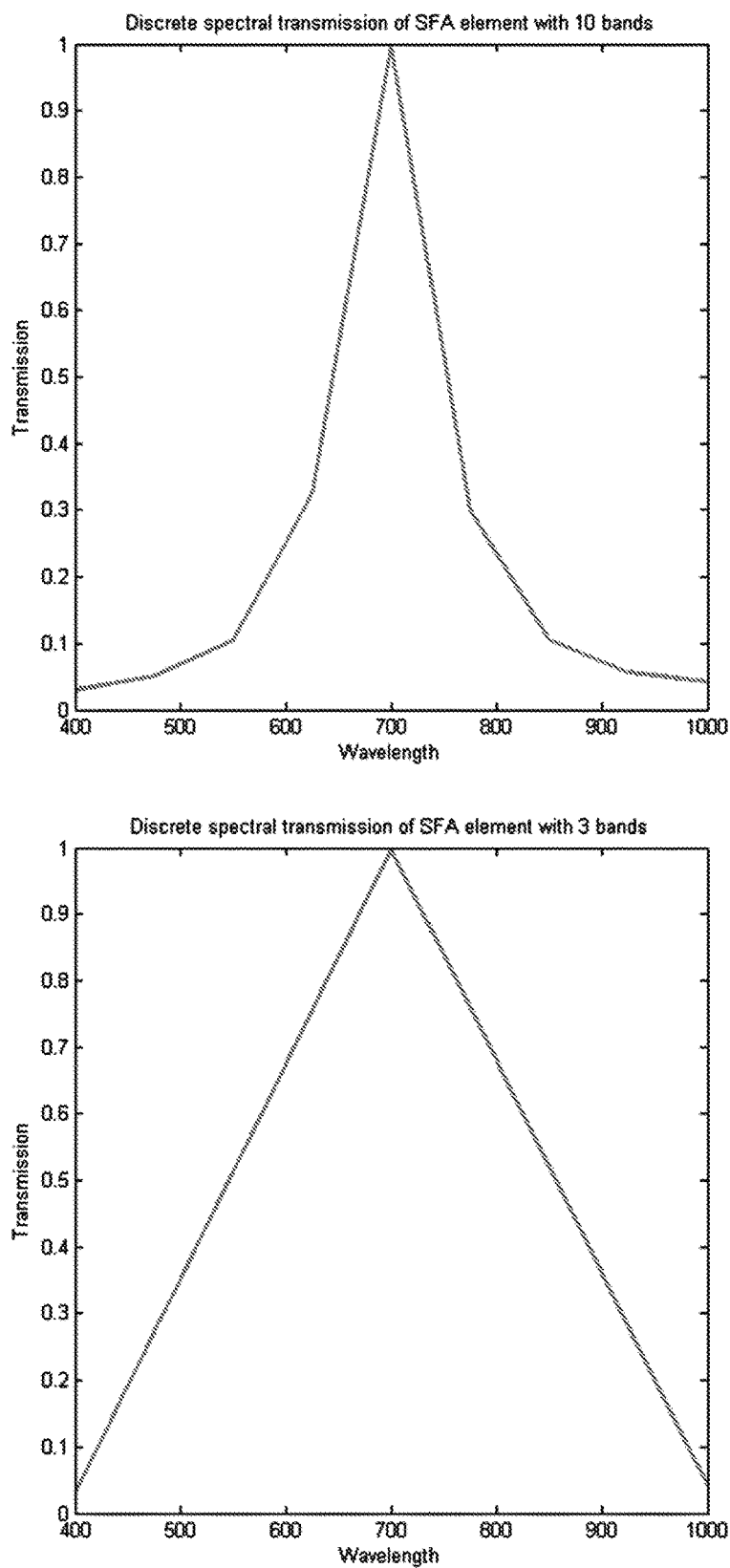

While the SFA elements sample the continuous incoming light spectrum, the design matrix A contains discrete versions of the SFA transmissions, whose spectral resolution will be equal to the number of spectral bands of the reconstructed data cube. This property allows for the reconstruction of a various number of spectral bands, this number having only a lower bound, dictated by the minimum number of bands required to properly represent the SFA element transmission curves. In FIGS. 5A and 5B, the effects of the aforementioned discretization and lower bound are depicted: while 30 and 10 bands produce an adequate representation of the SFA element transmission, 3 bands are insufficient.

Under the hypothesis of local spectral homogeneity of the imaged scene, the number of spectral samples in y can be artificially increased by pixel grouping, resulting in a non-diagonal system design matrix A. This hypothesis can be further enforced by the use of an anti-aliasing filter placed in front of the SFA. Each spatial pixel of the image sensor readout constitutes a single spectral sample of the complete spectral response of the corresponding point in the imaged scene. The reconstruction process may include the grouping of multiple spectral samples per pixel, which are derived from the spatial pixels in the close vicinity of the processed pixel.

One method for pixel grouping may be a sliding 2D window, which groups all spectral samples from pixels falling inside its area into the central pixel. If the SFA contains a periodic interleaved pattern, another method for pixel grouping may be guided by the contrast gradients observed in the dense image directly obtained from the pixels behind periodic elements. Using this dense image allows for grouping of pixels which do not span across edges or high contrast areas, thus reducing the possible artefacts produced by pixel grouping.

The variable resolution discrete filter representation and the pixel grouping methods described above work in unison to allow for the adjustment of the reconstructed hyperspectral data cube's spatial and spectral resolutions. Depending on the desired hyperspectral data cube resolution desired, only A and y need to be recomputed accordingly, while the hyperspectral imager configuration remains fixed.

Reconstruction of the hyperspectral cube can be achieved by applying regressive machine learning methods [12] such as neural networks or random forests to the sensor readout or pixel-grouped sensor readout. These methods take in an input signal or feature (y) and output an estimation of the original signal (x). Through training with a large number of examples, models such as neural networks can learn to un-mix and correct spectral data from the sensor readout.

Another method for reconstructing the hyperspectral data cube x from the measurements y can be modelled as a convex optimization problem:

$$\text{argmin}(\|Ax-y\|_2 + c(x)) \quad (2)$$

where the function c(x) is an always positive penalty term, constraining the search space for the optimal x based on a priori knowledge of the properties of x. The function c(x) will have low values for instances of x corresponding to a priori knowledge, while $\|Ax-y\|_2$ will have low values for instances of x fitting the measured data y. The convex optimisation (2) can thus be interpreted as finding the spectral data cube x which simultaneously best fits the measured data y and the a priori knowledge about its structure c(x).

Variations of the aforementioned reconstruction model include changing the representation of x to a mathematical basis in which x becomes sparse. For instance, basis such as Fourier, direct cosine transform, wavelet or gradient are known to be sparse for natural images [9]. In these cases, (2) may become:

$$\text{argmin}(\|ASx-y\|_2 + \lambda\|Sx\|_1) \quad (3)$$

where S is the matrix representation of the transformation from the chosen sparse mathematical basis and c(x) is replaced with the $L_1$ norm which enforces sparsity on the representation of x, while λ controls the strength of penalization. For hyperspectral data cubes, other transformations can be envisioned, such as projecting the measured data onto a known set of spectral vectors, obtained through principal component analysis, for instance.

The preferred implementation of the reconstruction algorithm is based on a version of the fast iterative shrinkage-thresholding algorithm (FISTA) introduced in [10], using the total variation (TV) norm as the penalty term. The reconstructed data cube is thus found by minimizing:

$$\text{argmin}(\|Ax-y\|_2 + \lambda\|x\|_{TV}) \quad (4)$$

where $\|x\|_{TV}$ can either be the 3D TV norm of the entire reconstructed hyperspectral data cube, or the sum of the 2D TV norms of the individual spectral bands of the reconstructed hyperspectral data cube. Using the sum of 2D TV norms rather than the 3D TV norm has the advantage of independently processing spectral bands and allowing for parallelization of the most computationally intensive steps of FISTA.

If the measurements y were produced by a system configuration having an anti-aliasing filter in the optical path, the quality and speed of the reconstruction produced by FISTA can be improved by independently blurring the spectral bands of the estimated reconstruction at each iteration of the algorithm, in an amount proportional to the blurring induced by the anti-aliasing filter. This process can be parallelized.

Figure 2A:
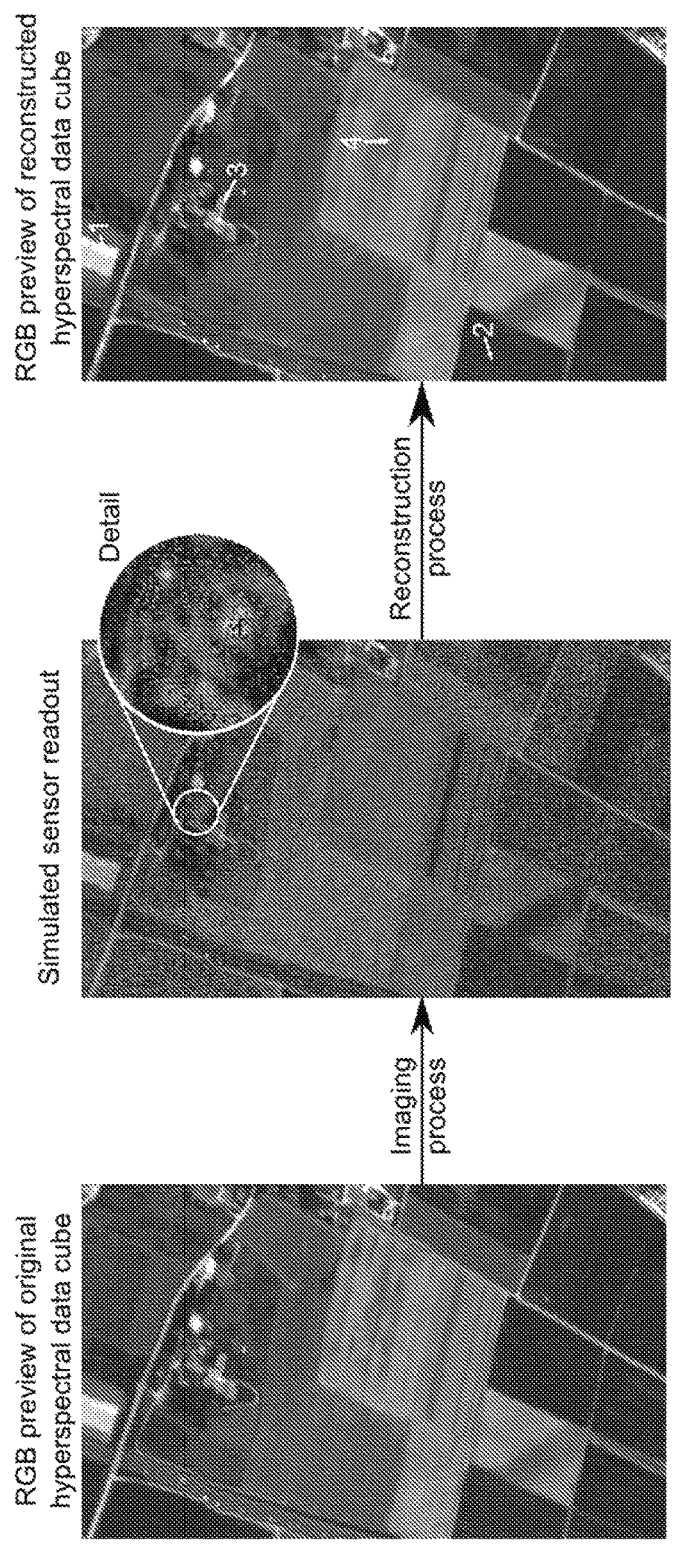
FIG. 2A shows a color preview of an aerial image scene, the corresponding sensor readout and the color preview of the reconstructed 100 band spectral data cube, as computed by a simulation. Four points of interest are marked on the reconstructed image.
Figure 2B:
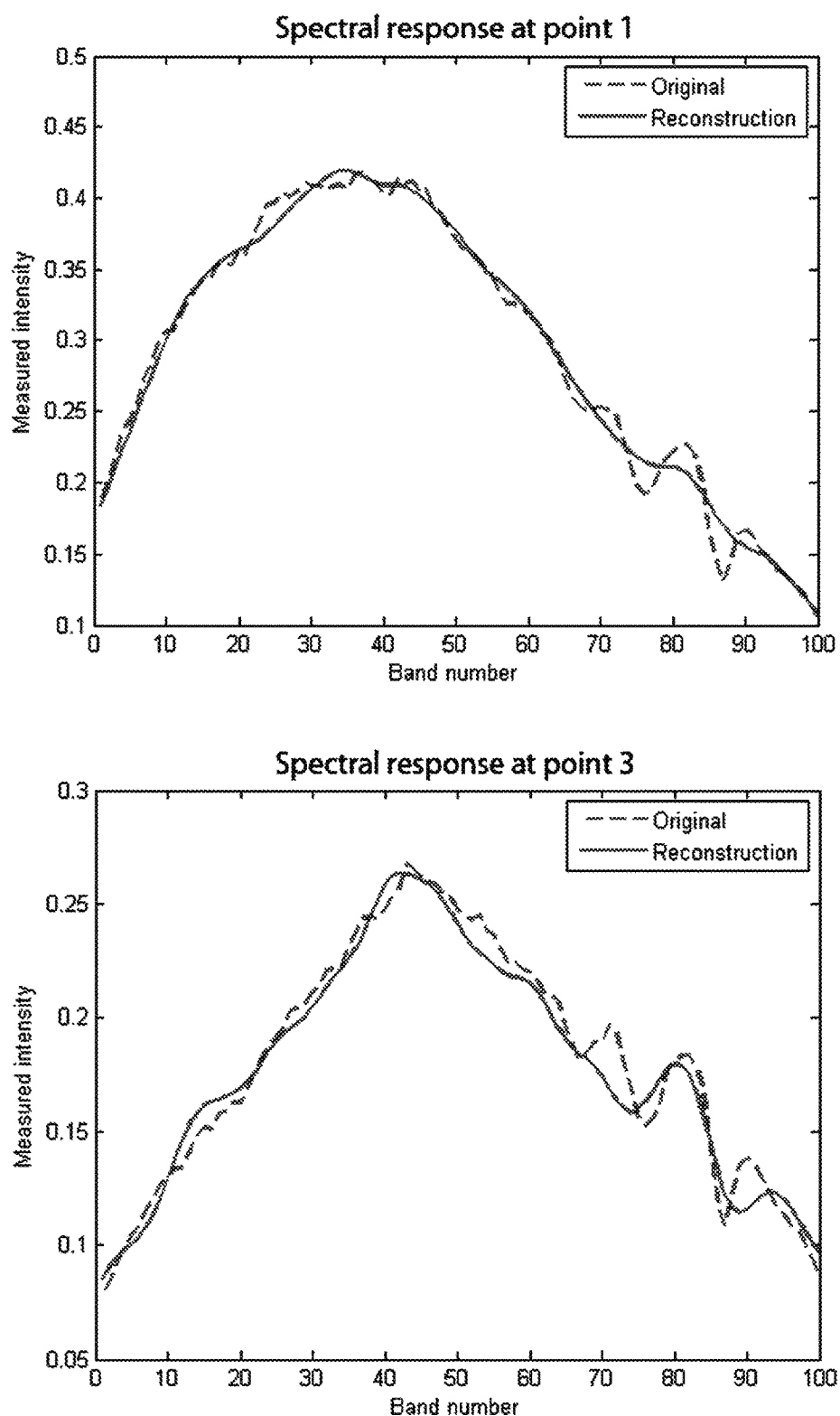
FIG. 2B-C shows a spectral comparison between the original image scene sampled at 100 bands (marked "Original") and the reconstructed spectral data cube (marked "Reconstructed"), for each of the four points marked in FIG. 2.

A simulation of the imaging and reconstruction process of the invention has been used to validate the principles of the present invention, the results of which are presented in FIGS. 2A and 2B. The target compression ratio was 1/100, meaning the hyperspectral data cube was reconstructed from 100 times fewer measurements than its total number of elements. A SFA model based on Wang tiling and Fabry-Perot filter transmissions was employed, containing 100 filters of central wavelengths between 400 and 1000 nm, and 100 nm full width at half maximum (FWHM). The SFA element's transmissions were discretized in 100 spectral bands. The SFA also contained a periodic pattern of elements having the central wavelength at 700 nm, as shown in FIGS. 3C and 5. Gradient-based pixel grouping was applied, grouping together 4 pixels from a vicinity of 5×5 pixels. FISTA was configured to minimize the sum of 2D TV norms of independent bands in parallel and included the blurring step at each iteration.

Figure 2C:
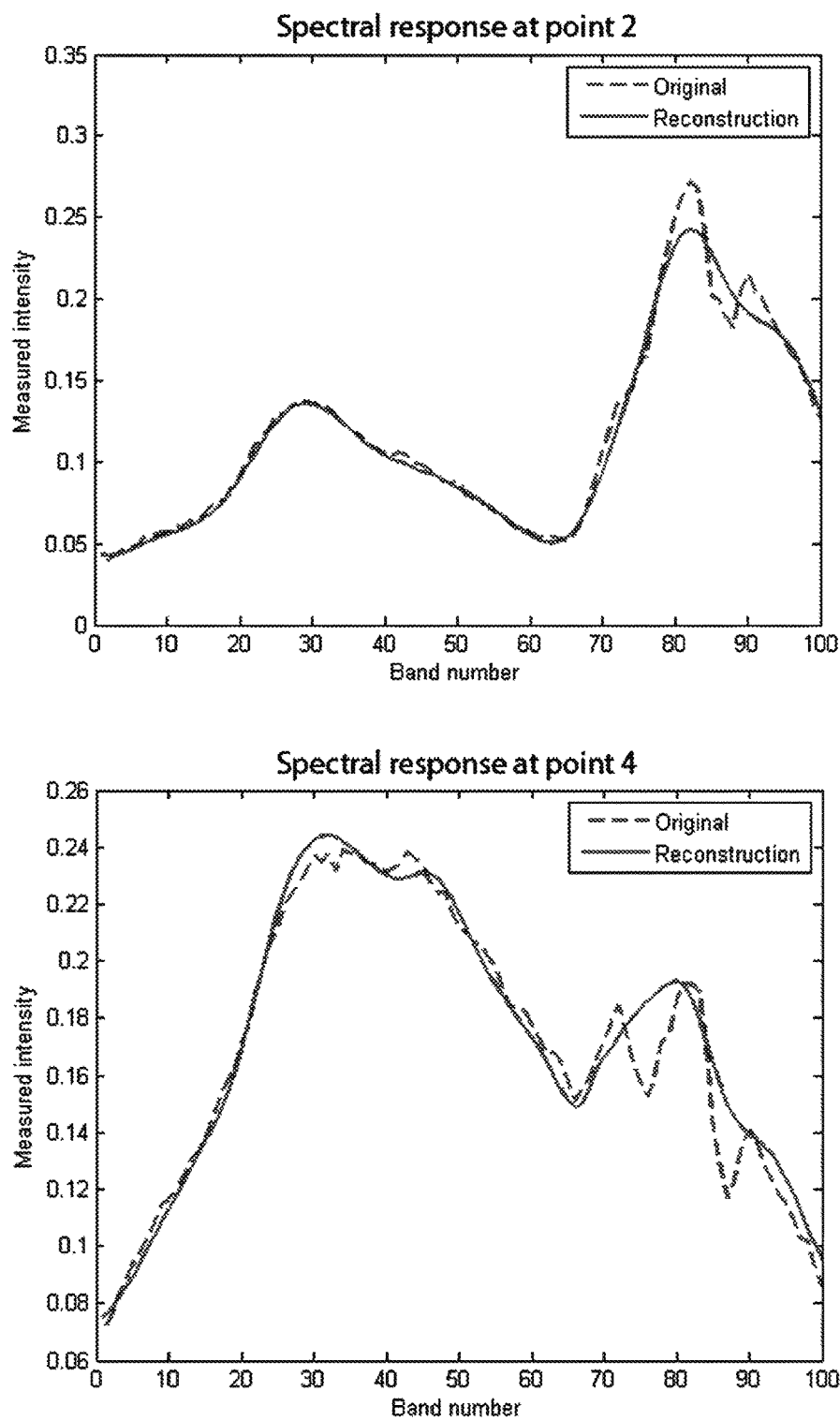

The obtained simulated sensor readout as well as a color preview of the hyperspectral data cube are shown in FIG. 2A. Four points of interest have been marked on the reconstructed image, presenting various spectral properties as well as being located in areas of various spatial detail across the imaged scene. The spectral properties of the original spatio-spectral image scene and the reconstructed hyperspectral data cube are compared in these four points, the results shown in FIGS. 2B and 2C. The spectral resolution is notable, where the reconstructed spectrum exhibits detail at much finer resolution than the FWHM of the SFA elements used to sample the spectrum. If a spectral camera with 100 nm wide filters at half-maximum had directly sampled such a spectrum, sharp spectral features such as peaks would have been smoothed out by these filters through the sampling process. However, in our reconstructions we clearly see sharp peaks and valleys spanning less than 10 bands (or 60 nm), well below the FWHM of the SFA elements used for the spectral sampling.

Commercial Applications

Imaging spectroscopy technology has numerous and proven applications in research and commercial domains, including agriculture, natural resource management, mineralogy, medicine and manufacturing among others. Specifically, the disclosed invention facilitates the development of a new class of compact, lightweight and inexpensive spectral imaging sensors. The new sensors are suitable for deployment using small unmanned aircraft systems, and cater for many of the existing applications, while facilitating a fundamentally new range of usage scenarios.

In particular, in the context of the agricultural and related industries the presented market size estimate is discussed in detail in [11].

Airborne spectral imaging constitutes the single most effective method of large-scale monitoring and analysis of vegetation with a proven capability in:

early detection, diagnosis and control of plant diseases;
stress detection and growth monitoring;
detection and control of invasive species.

Despite the many proven benefits, today's airborne spectral imaging technology is too expensive and complex for effective exploitation in the agricultural and related industries. In particular, none of the existing solutions has gained any significant traction in commercial farming applications thus far.

The proposed invention has the potential to make systematic spectral monitoring of vegetation accessible and highly profitable by reducing the cost of data acquisition and processing by a factor of 10, or more, while providing up to 10% increase in yield and associated revenues for the customers.

The available US statistics suggests 100 million hectares of prime croplands that may require systematic monitoring at a rate of 5 times a year or more. Approximately 10,000 spectral imaging systems are required in order to conduct the necessary monitoring. The resultant combined value of hardware of data processing services may be estimated as US $540 million for the USA market. Assuming the size of the global market to be five times the size of the USA market and taking into account other fields of application including environmental monitoring, forestry, control of invasive species, etc., results in an estimate for the total global market for airborne spectral vegetation monitoring of at least $2 billion.

Summarizing, the invention relates to the field of imaging spectroscopy, which is a method for optical sensing of both spatial and spectral image properties. Specifically, the invention describes a system and methodology to obtain spectral images, also known as spectral data cubes due to their three-dimensional nature comprised by two spatial and one spectral dimensions.

The described system is structurally simple and is designed to facilitate the manufacturing of a compact and lightweight spectral imaging camera. The system embodiment includes a lens, a 2D spectral filter array, a 2D imaging sensor, as well as the storage and the data processing mechanisms required to obtain a spectral image. Preferably the invention comprises the specific configuration of the spectral filter array comprised by spectral filters positioned in front of the individual light-sensitive elements of the image sensor. The invention further describes a computational framework utilized for the reconstruction of a 3D spectral data cube from the 2D dataset provided by the imaging sensor, as well as a real-time generation of a preview image. Algorithmic methods are also provided for variable spatio-spectral resolution reconstruction of the imaged scene, based on a fixed configuration imager.

REFERENCES

[1] Ellis, J., (2001) *Searching for oil seeps and oil-impacted soil with hyperspectral imagery*, Earth Observation Magazine.

[2] Lacar, F. M., et al., (2001) *Use of hyperspectral imagery for mapping grape varieties in the Barossa Valley, South Australia*, Geoscience and remote sensing symposium (IGARSS '01)—IEEE 2001 International, vol. 6 2875-2877 p.

[3] Tack, K., Lambrechts, A., Haspeslagh, L. (2011) Integrated circuit for spectral imaging system, Patent No. WO/2011/064403

[4] Lustig et al, (2007) *Sparse MRI: The Application of Compressed Sensing for Rapid MR Imaging*, MRM 58:1182-1195

[5] Singh, T., Singh, M. (2011) Method and System for Compressive Color Image Sampling and Reconstruction. Patent no. US20110142339 A1.

[6] A. Wagadarikar, R. John, R. Willett, and David Brady, (2008) *Single disperser design for coded aperture snapshot spectral imaging*, Appl. Opt. 47, B44-B51.

[7] Golbabaee, M., Vandergheynst, P., (2012) *Hyperspectral image compressed sensing via low-rank and joint-sparse matrix recovery*, IEEE International Conference on Acoustics, Speech and Signal Processing (ICASSP), p. 2741-2744

[8] Heikki, S., Ville-Veikko, A., Altti A., Tapani A., Christer H., Uula K., Jussi M., Jyrki O., (2009) *Novel miniaturized hyperspectral sensor for UAV and space applications*. Proc. SPIE 7474, Sensors, Systems, and Next-Generation Satellites XIII, 74741M, doi:10.1117/12.830284.

[9] Subhasis, S., (2000) *Image compression—from DCT to wavelets: a review*. Crossroads 6, doi:10.1145/331624.331630

[10] Beck, A., Teboulle, M., (2009) *Fast Gradient-Based Algorithms for Constrained Total Variation Image Denoising and Deblurring Problems*, IEEE Transactions on Image Processing, vol. 18, no. 11, pp. 2419, 2434, November 2009 doi:10.1109/TIP.2009.2028250

[11] The Economic Impact of Unmanned Aircraft Systems Integration in the United States, AUVSI, 2013

[12] T. M. Mitchell, "Machine Learning", 1997, ISBN: 0070428077 9780070428072

The invention claimed is:

1. A method for obtaining spectral imaging data, comprising the steps of:
   receiving a sample set of data generated by sampling a spectral property of an image of an object in a spatial basis, wherein the sampling of the spectral property of the image of the object comprises
   providing a Spectral Filter Array (SFA) by
   arranging a plurality of SFA elements together to form a surface,
   configuring each SFA element of the plurality of SFA elements to filter one or more spectral bandwidths centered each at specific wavelengths corresponding to that SFA element, wherein all of the plurality of SFA elements taken together cover a determined spectral range, and
   setting the specific wavelengths of each SFA element of the plurality of SFA elements on the surface such to obtain a statistically uniform and aperiodic spatial distribution of all of the plurality of SFA elements across the surface, optimizing for local uniformity and filling the surface with a repeating pattern of super-pixels, each super-pixel including a contiguous area of SFA elements including all unique SFA spectral transmissions, and continuously and randomly inter-changing the SFA elements inside of a respective super-pixel until a measured entropy of all the plurality of SFA elements central wavelengths converges to a value indicating a reaching of aperiodicity;
   providing an image sensor configured to record at each pixel the light filtered by one of the plurality of SFA elements or a subset of the plurality of SFA elements thereby producing one intensity value of light filtered by the one of the plurality of elements or the subset of the plurality of SFA elements per pixel,
   forming the image of the object on the SFA through a lens or group of lenses,
   recording for all of the pixels of the image sensor the spectrally filtered intensity values thereby obtaining a 2-dimensional array of the intensity values corresponding to the image of the object,
   reconstructing a full 3 dimensional spectral data cube of the imaged object from the sampled 2-dimensional array.

2. The method of claim 1, wherein the step of reconstructing comprises:
   creating a mathematical model as a simple or convolutional neural network;
   training the convolutional neural network on a number of pairs of dense 3 dimensional spectral data cubes and synthetically generated sparsely and uniformly sampled spectral imaging data, such that the convolutional neural network learns an interpolation function; and
   applying the trained convolutional neural network on the sparsely and uniformly sampled spectral imaging data.

3. The method of claim 2, wherein the step of reconstructing further comprises:
   a convex optimization method based on measurements of the spectral transmission of every pixel from the sparsely and uniformly sampled spectral imaging data.

4. The method of claim 1, wherein the step of reconstructing further comprises:

creating the mathematical model as a system design matrix from measured transmissions of every pixel from the sparsely and uniformly sampled spectral imaging data; and inferring non sampled spectral information using deconvolution or non-linear sparse reconstruction methods based on the system design matrix.

5. The method of claim 1, wherein the step of setting the specific wavelengths of each SFA element of the plurality of SFA elements on the surface such to obtain the statistically uniform and aperiodic spatial distribution of the specific wavelengths of the SFA is deterministic, and includes an aperiodic tiling method.

6. The method of claim 1, further comprising the steps of:
setting a specific spectral response of each SFA element of the plurality of SFA elements on the surface such to obtain the multiband spectral response distribution of the specific wavelengths of the SFA by
providing a plurality of multiband SFA elements such that neighboring SFA elements are spectrally orthogonal,
providing a plurality of multiband SFA elements such that each SFA element is sensitive in a number of spectral ranges covering a subset of the desired spectral range, and
providing a plurality of multiband SFA elements such that the collection of the sensitive ranges of the individual SFA elements cover the entire desired spectral range.

7. A method for obtaining a real-time monochromatic preview of an imaged object, the imaged object having been obtained using the method of obtaining spectral imaging data of claim 1, the method for obtaining the real-time monochromatic preview comprising the steps of:
designing a uniform aperiodic Spectral Filter Array (SFA) by arranging a plurality of SFA elements together to form a surface, configuring each SFA element of the plurality of SFA elements to filter a spectral bandwidth centered at a central wavelength corresponding to that SFA element, whereby all of the plurality of SFA elements taken together cover a determined spectral range, and setting the central wavelength of each SFA element of the plurality of SFA elements on the surface such to obtain a distribution of all the central wavelengths to be uniform and aperiodic over the surface,
generating a subset of SFA elements by a 2-dimensional periodic selection,
replacing the SFA elements belonging to the above subset with SFA elements of identical transmission, and
from a 2-dimensional array of pixel intensity values, using a subset of values, corresponding to the subset of periodic SFA elements with identical transmission, to create a lower resolution monochromatic image.

8. A method for obtaining a real-time monochromatic preview of an imaged object, the imaged object having been obtained using the method of obtaining spectral imaging data of claim 1, the method for obtaining the real-time monochromatic preview comprising the steps of:
designing a uniform aperiodic Spectral Filter Array (SFA) by arranging a plurality of SFA elements together to form a surface, configuring each SFA element of the plurality of SFA elements to filter multiple spectral bands centered at specific wavelengths corresponding to that SFA element, whereby all of the plurality of SFA elements taken together cover a determined spectral range, and setting the central wavelength of each SFA element of the plurality of SFA elements on the surface such that neighboring SFA elements are spectrally orthogonal, from a 2-dimensional array of pixel intensity values, spatially interpolating each channel corresponding to an SFA element configuration independently at pixel locations where other SFA element configurations are present, and averaging the independently interpolated channels, to create a high resolution monochromatic image.

9. A non-transitory computer readable medium having a computer-executable program stored thereon, the computer-executable program, when executed by a computing device, configured to perform a method according to claim 1 to reconstruct a 3D-hyperspectral image from a 2D-spatial-spectral dataset.

10. A method for Spectral Filter Array (SFA) element second-degree transmission cancellation through SFA design and subsequent response subtraction comprising at least:
designing a uniformly and aperiodically distributed Spectral Filter Array (SFA) by
arranging a plurality of SFA elements together to form a surface,
configuring each SFA element of the plurality of SFA elements to filter a spectral bandwidth centered at a central wavelength corresponding to that SFA element, whereby all of the plurality of elements taken together cover a determined spectral range, and
setting the central wavelength of each SFA element of the plurality of SFA elements on the surface such to obtain a distribution of all the central wavelengths to be uniform and aperiodic over the surface;
identifying the SFA elements with second degree transmission in the sensitivity range of an image sensor,
changing the central wavelength of SFA elements neighboring the SFA elements with second degree transmission, as to match the central wavelength of the second degree transmission,
re-arranging the SFA element central wavelengths which were not changed or do not have a second degree transmission, as to maintain the uniformity of the SFA central wavelength distribution, and
in a 2-dimensional array of pixel intensity values, subtracting the response corresponding to the changed neighboring elements from the response corresponding to the SFA elements which have a second degree transmission.

11. A non-transitory computer readable medium having a computer-executable program stored thereon, the computer-executable program, when executed by a computing device, configured to perform a method according to claim 10 to cancel SFA element second-degree transmission through SFA design and subsequent response subtraction.

12. A method for generating a spectral 3D-model of an imaged object and increasing the spectral reconstruction quality of an imaged scene, comprising:
taking multiple images of the scene, each of the images comprising at least an array of pixel intensities,
using monochromatic previews to optically align the images through image registration, thus generating the 3D-model of the scene,
grouping values from different ones of the arrays of pixel intensities corresponding to different images of the multiple images, if the pixels are aligned to a same point in the imaged scene,
based on grouped values, re-modeling a system design matrix corresponding to multiple arrays of pixel intensities, taken from different locations, and reconstructing the spectral texture of the 3D model based on the cross-image system design matrix.

13. A non-transitory computer readable medium having a computer-executable program stored thereon, the computer-executable program, when executed by a computing device, configured to perform a method according to claim 12 to generate a spectral 3D-model of an imaged object and increasing the spectral reconstruction quality of an imaged scene.

* * * * *